US010272656B2

(12) United States Patent
Miller, II (10) Patent No.: US 10,272,656 B2
(45) Date of Patent: Apr. 30, 2019

(54) METHOD FOR MAKING A MULTILAYER ADHESIVE LAMINATE (71) Applicant: MYLAN INC., Morgantown, WV (US)

(72) Inventor: Kenneth J. Miller, II, Uniontown, PA (US)

(73) Assignee: Mylan Inc., Canonsburg, PA (US)

(*) Notice: Subject to any disclaimer, the term of this patent is extended or adjusted under 35 U.S.C. 154(b) by 122 days.

(21) Appl. No.: 15/626,663

(22) Filed: Jun. 19, 2017

(65) Prior Publication Data
US 2017/0282526 A1 Oct. 5, 2017

Related U.S. Application Data (63) Continuation of application No. 13/299,747, filed on Nov. 18, 2011, now Pat. No. 9,731,490, which is a
(Continued)

(51) Int. Cl.
B32B 38/00 (2006.01)
B32B 37/00 (2006.01)
(Continued)

(52) U.S. Cl.
CPC ............ B32B 37/02 (2013.01); B32B 38/04 (2013.01); B32B 38/1816 (2013.01); C09J 7/00 (2013.01);
(Continued)

(58) Field of Classification Search
CPC . B32B 38/04; B32B 38/1816; B32B 37/0053; B32B 2038/045; C09J 7/0207;
(Continued)

(56) References Cited

U.S. PATENT DOCUMENTS 2,511,559 A 6/1950 Banff et al.
2,649,131 A 8/1953 Lincoln
(Continued)

FOREIGN PATENT DOCUMENTS

AU 200038096 10/2000
DE 4 018 057 12/1991
(Continued)

OTHER PUBLICATIONS

Abstract for DE 4018057.
(Continued)

Primary Examiner — Linda L Gray (57) ABSTRACT

A method allows for rapid manufacture of relatively thick adhesive coatings using a continuous process, where a single thin coating is continuously converted into a single thicker adhesive laminate. An exemplary process includes the steps of: (1) producing a web having a first surface with an adhesive layer and a second surface with a release liner; (2) slitting the web longitudinally into a first section and a second section; (3) laminating a backing film to the adhesive layer of the first section; (4) removing the release liner of the laminate of step (3) exposing the adhesive layer of the first section; and (5) laminating the second section to the laminate of step (4), wherein the adhesive layer of the laminate of step (4) is combined with the adhesive layer of the second section.

12 Claims, 10 Drawing Sheets

Related U.S. Application Data continuation of application No. 12/571,560, filed on Oct. 1, 2009, now Pat. No. 8,142,592.

(60) Provisional application No. 61/102,223, filed on Oct. 2, 2008.

(51) Int. Cl.

| | | |
|---|---|---|
| *C09J 7/00* | (2018.01) | |
| *A61F 13/00* | (2006.01) | |
| *B32B 37/02* | (2006.01) | |
| *B32B 38/04* | (2006.01) | |
| *B32B 38/18* | (2006.01) | |
| *C09J 7/38* | (2018.01) | |
| *C09J 7/10* | (2018.01) | |
| *A61F 13/02* | (2006.01) | |

(52) U.S. Cl.
CPC . *C09J 7/10* (2018.01); *C09J 7/38* (2018.01); *A61F 13/0253* (2013.01); *B32B 37/0053* (2013.01); *B32B 2038/045* (2013.01); *C09J 2201/36* (2013.01); *C09J 2201/606* (2013.01); *Y10T 156/1059* (2015.01); *Y10T 156/1062* (2015.01); *Y10T 156/1069* (2015.01); *Y10T 156/1075* (2015.01); *Y10T 156/1077* (2015.01)

(58) Field of Classification Search
CPC .............. C09J 7/00; Y10T 156/1069; Y10T 156/1059; Y10T 156/1075; Y10T 156/1077; Y10T 156/1962; A61F 13/00051; A61F 13/00063; A61F 13/00085; A61F 13/0253; A61F 2013/0089; A61F 2013/00217; A61F 2013/00106; A61F 2013/00102; A61F 2013/0296; A61K 9/7053
See application file for complete search history.

(56) References Cited

U.S. PATENT DOCUMENTS

| | | |
|---|---|---|
| 3,247,042 A | 4/1966 | Denton et al. |
| 3,566,752 A | 3/1971 | Dreher |
| 3,632,386 A | 1/1972 | Hurst |
| 3,639,500 A | 2/1972 | Muny et al. |
| 3,655,475 A | 4/1972 | Stelling, Jr. et al. |
| 3,744,383 A | 7/1973 | Finch et al. |
| 3,993,815 A | 11/1976 | Douek et al. |
| 4,039,705 A | 8/1977 | Douek et al. |
| 4,104,816 A | 8/1978 | Pingeton |
| 4,163,684 A | 8/1979 | Kartanson |
| 4,201,613 A | 5/1980 | Olivieri et al. |
| 4,285,999 A | 8/1981 | Olivieri et al. |
| 4,398,985 A | 8/1983 | Eagon |
| 4,614,076 A | 9/1986 | Rathemacher |
| 4,759,816 A | 7/1988 | Kasper et al. |
| 4,837,088 A | 6/1989 | Freedman |
| 4,891,260 A | 1/1990 | Kunkel et al. |
| 4,940,579 A | 7/1990 | Randen |
| 4,994,278 A | 2/1991 | Sablotsky et al. |
| 4,995,933 A | 2/1991 | Brüssel |
| 5,019,204 A | 5/1991 | Brüssel |
| 5,082,663 A | 1/1992 | Konishi et al. |
| 5,085,866 A | 2/1992 | Cowsar et al. |
| 5,120,544 A | 6/1992 | Henley |
| 5,135,798 A | 8/1992 | Muschter et al. |
| 5,143,570 A | 9/1992 | Freedman |
| 5,234,957 A | 8/1993 | Mantelle |
| 5,288,714 A | 2/1994 | Marschke |
| 5,306,504 A | 4/1994 | Lorenz |
| 5,332,576 A | 7/1994 | Mantelle |
| 5,362,516 A | 11/1994 | Wilson et al. |
| 5,368,860 A | 11/1994 | Sunami et al. |
| 5,370,941 A | 12/1994 | Kiang |
| 5,383,511 A | 1/1995 | Marasco |
| 5,405,366 A | 4/1995 | Fox et al. |
| 5,411,738 A | 5/1995 | Hind |
| 5,446,070 A | 8/1995 | Mantelle |
| 5,476,712 A | 12/1995 | Hartman et al. |
| 5,514,240 A | 5/1996 | Hagiiiri-Teiirani et al. |
| 5,516,581 A | 5/1996 | Kreckel et al. |
| 5,536,263 A | 7/1996 | Rolf et al. |
| 5,558,913 A | 9/1996 | Sasaki et al. |
| 5,588,962 A | 12/1996 | Nicholas et al. |
| 5,589,122 A | 12/1996 | Leonard et al. |
| 5,589,180 A | 12/1996 | Hind |
| 5,589,192 A | 12/1996 | Okabe et al. |
| 5,597,437 A | 1/1997 | Lange et al. |
| 5,601,838 A | 2/1997 | Hind |
| 5,601,839 A | 2/1997 | Quan et al. |
| 5,656,286 A | 8/1997 | Miranda et al. |
| 5,686,099 A | 11/1997 | Sablotsky et al. |
| 5,709,869 A | 1/1998 | Hind |
| 5,719,197 A | 2/1998 | Kanios et al. |
| 5,741,510 A | 4/1998 | Rolf et al. |
| 5,744,162 A | 4/1998 | Okabe et al. |
| 5,776,287 A | 7/1998 | Best et al. |
| 5,776,952 A | 7/1998 | Liedtke |
| 5,810,786 A | 9/1998 | Jackson et al. |
| 5,827,529 A | 10/1998 | Ono et al. |
| 5,830,497 A | 11/1998 | Yamanaka et al. |
| 5,834,010 A | 11/1998 | Quan et al. |
| 5,840,755 A | 11/1998 | Liedtke |
| 5,900,245 A | 5/1999 | Sawhney et al. |
| 5,958,446 A | 9/1999 | Miranda et al. |
| 6,004,665 A | 12/1999 | Luhmann et al. |
| 6,059,913 A | 5/2000 | Asmussen et al. |
| 6,096,333 A | 8/2000 | Rolf et al. |
| 6,096,334 A | 8/2000 | Rolf et al. |
| 6,110,488 A | 8/2000 | Hoffmann |
| 6,117,437 A | 9/2000 | Roreger |
| 6,120,792 A | 9/2000 | Juni |
| 6,190,689 B1 | 2/2001 | Hoffmann et al. |
| 6,207,184 B1 | 3/2001 | Ikeda et al. |
| 6,218,006 B1 | 4/2001 | Tokunaga et al. |
| 6,280,840 B1 | 8/2001 | Luhmann et al. |
| 6,299,902 B1 | 10/2001 | Jun et al. |
| 6,313,370 B1 | 11/2001 | Hyson |
| 6,331,336 B1 | 12/2001 | Szonn et al. |
| 6,361,790 B1 | 3/2002 | Rolf et al. |
| 6,365,178 B1 | 4/2002 | Venkateshwaran et al. |
| 6,383,511 B1 | 5/2002 | Cassel |
| 6,420,309 B1 | 7/2002 | Grime et al. |
| 6,429,228 B1 | 8/2002 | Inagi et al. |
| 6,436,530 B1 | 8/2002 | Szonn et al. |
| 6,447,787 B1 | 9/2002 | Gassner et al. |
| 6,455,066 B1 | 9/2002 | Fischer et al. |
| 6,461,644 B1 | 10/2002 | Jackson et al. |
| 6,469,227 B1 | 10/2002 | Cooke et al. |
| 6,503,620 B1 | 1/2003 | Xie et al. |
| 6,528,086 B2 | 3/2003 | Zhang |
| 6,541,098 B2 | 4/2003 | Venkatasanthanam et al. |
| 6,544,615 B2 | 4/2003 | Otten et al. |
| 6,582,724 B2 | 6/2003 | Hsu et al. |
| 6,586,000 B2 | 7/2003 | Luo et al. |
| 6,627,030 B2 | 9/2003 | Yang et al. |
| 6,627,620 B1 | 9/2003 | Nielsen |
| 6,630,486 B1 | 10/2003 | Royer |
| 6,645,521 B2 | 11/2003 | Cassel |
| 6,663,932 B2 | 12/2003 | McLaughlin et al. |
| 6,663,947 B2 | 12/2003 | Freedman et al. |
| 6,673,363 B2 | 1/2004 | Luo et al. |
| 6,682,757 B1 | 1/2004 | Wright |
| 6,713,144 B2 | 3/2004 | Bundo et al. |
| 6,740,379 B1 | 5/2004 | Congard et al. |
| 6,746,689 B2 | 6/2004 | Fischer et al. |
| 6,761,895 B2 | 7/2004 | Sawada et al. |
| 6,767,425 B2 | 7/2004 | Meier |
| 6,808,642 B2 | 10/2004 | Takaya et al. |
| 6,818,226 B2 | 11/2004 | Reed et al. |
| 6,835,256 B2 | 12/2004 | Menzies et al. |
| 6,861,068 B2 | 3/2005 | Ng et al. |

(56) References Cited

U.S. PATENT DOCUMENTS

| | | |
|---|---|---|
| 6,871,477 B1 | 3/2005 | Tucker |
| 6,953,513 B1 | 10/2005 | Volkert |
| 6,953,590 B1 | 10/2005 | Owaki et al. |
| 6,980,854 B2 | 12/2005 | Bernabei |
| 6,998,109 B1 | 2/2006 | Pearson et al. |
| 7,018,647 B1 | 3/2006 | Yamasaki et al. |
| 7,022,343 B2 | 4/2006 | Philbrook et al. |
| 7,029,693 B2 | 4/2006 | Hori et al. |
| 7,063,859 B1 | 6/2006 | Kanios et al. |
| 7,094,228 B2 | 8/2006 | Zhang et al. |
| 7,101,825 B2 | 9/2006 | Francis et al. |
| 7,109,161 B1 | 9/2006 | Gayed |
| 7,186,260 B2 | 3/2007 | Hyson |
| 7,241,357 B2 | 7/2007 | Roth et al. |
| 7,264,870 B2 | 9/2007 | Luhmann et al. |
| 7,311,954 B2 | 12/2007 | Koops et al. |
| 7,335,379 B2 | 2/2008 | Carrara et al. |
| 7,458,982 B2 | 12/2008 | Kraft et al. |
| 7,476,400 B2 | 1/2009 | Patel |
| 7,479,132 B2 | 1/2009 | Fukuta et al. |
| 7,537,590 B2 | 5/2009 | Santini, Jr. et al. |
| 7,572,613 B2 | 8/2009 | Klein |
| 7,582,783 B2 | 9/2009 | Blum |
| 2001/0021451 A1 | 9/2001 | Tokunaga et al. |
| 2002/0004065 A1 | 1/2002 | Kanios |
| 2002/0033225 A1 | 3/2002 | Becker et al. |
| 2002/0051875 A1 | 5/2002 | Luhmann et al. |
| 2002/0098347 A1 | 7/2002 | Szonn et al. |
| 2002/0110585 A1 | 8/2002 | Godbey et al. |
| 2002/0132008 A1 | 9/2002 | Mumper |
| 2002/0142042 A1 | 10/2002 | Mumper |
| 2002/0176841 A1 | 11/2002 | Barker et al. |
| 2003/0026932 A1 | 2/2003 | Johnson et al. |
| 2003/0027833 A1 | 2/2003 | Cleary et al. |
| 2003/0069318 A1 | 4/2003 | Dang et al. |
| 2003/0082225 A1 | 5/2003 | Mason |
| 2003/0082227 A1 | 5/2003 | Sournac et al. |
| 2003/0138503 A1 | 7/2003 | Staniforth et al. |
| 2003/0148949 A1 | 8/2003 | Podolsky et al. |
| 2003/0180347 A1 | 9/2003 | Young et al. |
| 2004/0013747 A1 | 1/2004 | Tucker |
| 2004/0028744 A1 | 2/2004 | Tongaree et al. |
| 2004/0072792 A1 | 4/2004 | Haraguchi et al. |
| 2004/0081685 A1 | 4/2004 | Wright |
| 2004/0101557 A1 | 5/2004 | Gibson et al. |
| 2004/0131665 A1 | 7/2004 | Wepfer |
| 2004/0214215 A1 | 10/2004 | Yu et al. |
| 2005/0002996 A1 | 1/2005 | Sojka |
| 2005/0003012 A1 | 1/2005 | Woller et al. |
| 2005/0019385 A1 | 1/2005 | Houze |
| 2005/0037200 A1 | 2/2005 | Wallach |
| 2005/0042173 A1 | 2/2005 | Besse et al. |
| 2005/0112183 A1 | 5/2005 | Galer |
| 2005/0115663 A1 | 6/2005 | Winkler |
| 2005/0202073 A1 | 9/2005 | Jackson et al. |
| 2005/0214376 A1 | 9/2005 | Faure et al. |
| 2005/0226910 A1 | 10/2005 | Sintov et al. |
| 2005/0228336 A1 | 10/2005 | Keusch et al. |
| 2005/0271729 A1 | 12/2005 | Wang |
| 2005/0281881 A1 | 12/2005 | Woeller et al. |
| 2006/0029654 A1 | 2/2006 | Cassel |
| 2006/0034904 A1 | 2/2006 | Weimann |
| 2006/0078604 A1 | 4/2006 | Kanios et al. |
| 2006/0088579 A1 | 4/2006 | Shastri et al. |
| 2006/0093673 A1 | 5/2006 | Coury |
| 2006/0178354 A1 | 8/2006 | Lucas |
| 2006/0188449 A1 | 8/2006 | Hirsh et al. |
| 2006/0193789 A1 | 8/2006 | Tamarkin et al. |
| 2006/0194759 A1 | 8/2006 | Eidelson |
| 2006/0198815 A1 | 9/2006 | Barker et al. |
| 2006/0198891 A1 | 9/2006 | Ravenelle et al. |
| 2006/0205678 A1 | 9/2006 | Gaeta et al. |
| 2006/0210613 A1 | 9/2006 | Carliss |
| 2006/0216245 A1 | 9/2006 | Haraguchi et al. |
| 2006/0240084 A1 | 10/2006 | Serafica et al. |
| 2006/0251890 A1 | 11/2006 | Lane et al. |
| 2006/0270736 A1 | 11/2006 | Pacheco |
| 2006/0293217 A1 | 12/2006 | Barker et al. |
| 2007/0042027 A1 | 2/2007 | Haley |
| 2007/0086955 A1 | 4/2007 | Kerdar et al. |
| 2007/0110805 A1 | 5/2007 | Levinson et al. |
| 2007/0166362 A1 | 7/2007 | Sakuma et al. |
| 2007/0166364 A1 | 7/2007 | Beier et al. |
| 2007/0203079 A1 | 8/2007 | Caldwell et al. |
| 2007/0207193 A1 | 9/2007 | Zasler et al. |
| 2007/0232985 A1 | 10/2007 | Sirkar et al. |
| 2007/0244294 A1 | 10/2007 | Pavlin |
| 2007/0248654 A1 | 10/2007 | Haley |
| 2007/0248655 A1 | 10/2007 | Haley |
| 2007/0264339 A1 | 11/2007 | Shah et al. |
| 2007/0269465 A9 | 11/2007 | Fita |
| 2007/0280972 A1 | 12/2007 | Zhang et al. |
| 2008/0015210 A1 | 1/2008 | Shah et al. |
| 2008/0021068 A1 | 1/2008 | Alam et al. |
| 2008/0114098 A1 | 5/2008 | Griswold et al. |
| 2008/0114284 A1 | 5/2008 | Anderson et al. |
| 2008/0145434 A1 | 6/2008 | Anderson et al. |
| 2008/0154210 A1 | 6/2008 | Jordan et al. |
| 2008/0166413 A1 | 7/2008 | Staniforth et al. |
| 2008/0182841 A1 | 7/2008 | Levine et al. |
| 2008/0206371 A1 | 8/2008 | Fontaine et al. |
| 2008/0220068 A1 | 9/2008 | Masini-eteve et al. |
| 2008/0233177 A1 | 9/2008 | Meconi |
| 2008/0255521 A1 | 10/2008 | Kubo et al. |
| 2008/0274164 A1 | 11/2008 | Vollmer |
| 2008/0286349 A1 | 11/2008 | Nomoto et al. |
| 2008/0287866 A1 | 11/2008 | Heller |
| 2008/0293015 A1 | 11/2008 | Wong et al. |
| 2008/0293703 A1 | 11/2008 | Richlin et al. |
| 2008/0299172 A1 | 12/2008 | Young et al. |
| 2008/0305155 A1 | 12/2008 | Jackson et al. |
| 2008/0317729 A1 | 12/2008 | Kasch et al. |
| 2008/0317863 A1 | 12/2008 | Nystrom et al. |
| 2009/0004281 A1 | 1/2009 | Nghiem et al. |
| 2009/0012067 A1 | 1/2009 | Rossetti et al. |
| 2009/0017125 A1 | 1/2009 | Lynenskjold et al. |
| 2009/0022801 A1 | 1/2009 | Vachon |
| 2009/0035377 A1 | 2/2009 | Houze |
| 2009/0036491 A1 | 2/2009 | Tucker et al. |
| 2009/0048296 A1 | 2/2009 | Campbell et al. |
| 2009/0048347 A1 | 2/2009 | Cohen et al. |
| 2009/0053290 A1 | 2/2009 | Sand et al. |
| 2009/0093547 A1 | 4/2009 | Corbitt et al. |
| 2009/0093669 A1 | 4/2009 | Farone et al. |
| 2009/0123527 A1 | 5/2009 | Alam et al. |
| 2009/0123528 A1 | 5/2009 | Fossel |
| 2009/0137473 A1 | 5/2009 | Martin et al. |
| 2009/0142401 A1 | 6/2009 | Appel et al. |
| 2009/0155235 A1 | 6/2009 | Cevc et al. |
| 2009/0162407 A1 | 6/2009 | Biggs et al. |
| 2009/0191127 A1 | 7/2009 | Saini |
| 2009/0196936 A1 | 8/2009 | John et al. |

FOREIGN PATENT DOCUMENTS

| | | |
|---|---|---|
| EP | 0331392 A2 | 9/1989 |
| EP | 0387751 A2 | 9/1990 |
| EP | 0388306 A2 | 9/1990 |
| EP | 0507160 A1 | 10/1992 |
| EP | 0582727 A1 | 2/1994 |
| EP | 0583244 B1 | 2/1994 |
| EP | 0674913 A2 | 10/1995 |
| EP | 0737066 B1 | 10/1996 |
| EP | 1329225 A2 | 7/2003 |
| EP | 1572157 | 9/2005 |
| EP | 1582220 A1 | 10/2005 |
| EP | 1702597 A2 | 9/2006 |
| JP | 59059612 | 4/1984 |
| JP | 59059613 | 4/1984 |
| JP | 59067218 | 4/1984 |
| JP | 61093113 | 5/1986 |
| JP | 61267510 | 11/1986 |
| JP | 61267512 | 11/1986 |
| JP | 62153227 | 7/1987 |

(56) References Cited

FOREIGN PATENT DOCUMENTS

| | | |
|---|---|---|
| JP | 63132824 | 6/1988 |
| JP | 63203630 | 8/1988 |
| JP | 63313723 | 12/1988 |
| JP | 01299216 | 12/1989 |
| JP | 02071745 | 3/1990 |
| JP | 04247027 | 9/1992 |
| JP | 05170644 | 7/1993 |
| JP | 05310559 | 11/1993 |
| JP | 06072880 | 3/1994 |
| JP | 06145051 | 5/1994 |
| JP | 07076526 | 3/1995 |
| JP | 07157424 | 6/1995 |
| JP | 07215850 | 8/1995 |
| JP | 07233054 | 9/1995 |
| JP | 07277961 | 10/1995 |
| JP | 07309756 | 11/1995 |
| JP | 08225448 | 9/1996 |
| JP | 09255565 | 9/1997 |
| JP | 10147521 | 6/1998 |
| JP | 2001302501 | 10/2001 |
| JP | 2005126341 | 5/2005 |
| JP | 2006248996 | 9/2006 |
| WO | WO 1996/033678 | 10/1996 |
| WO | WO 1998/017263 | 4/1998 |
| WO | WO 2000/012172 | 3/2000 |
| WO | WO 2000/056290 | 9/2000 |
| WO | WO 2001/039754 | 6/2001 |
| WO | WO 2001/041746 | 6/2001 |
| WO | WO 2001/047559 | 7/2001 |
| WO | WO 2002/017881 | 3/2002 |
| WO | WO 2002/051382 | 7/2002 |
| WO | WO 2003/011214 | 2/2003 |
| WO | WO 2003/020824 | 3/2003 |
| WO | WO 2003/066130 | 8/2003 |
| WO | WO 2003/077885 | 9/2003 |
| WO | WO 2003/099293 | 12/2003 |
| WO | WO 2004/047819 | 6/2004 |
| WO | WO 2004/060447 | 7/2004 |
| WO | WO 2004/080441 | 9/2004 |
| WO | WO 2004/103260 | 12/2004 |
| WO | WO 2004/105868 | 12/2004 |
| WO | WO 2004/110423 | 12/2004 |
| WO | WO 2005/037336 | 4/2005 |
| WO | WO 2005/042055 | 5/2005 |
| WO | WO 2005/055977 | 6/2005 |
| WO | WO 2005/092300 | 10/2005 |
| WO | WO 2005/110626 | 11/2005 |
| WO | WO 2005/113608 | 12/2005 |
| WO | WO 2005/123046 | 12/2005 |
| WO | WO 2006/017632 | 2/2006 |
| WO | WO 2006/017852 | 2/2006 |
| WO | WO 2006/039961 | 4/2006 |
| WO | WO 2006/044206 | 4/2006 |
| WO | WO 2006/084911 | 8/2006 |
| WO | WO 2006/085101 | 8/2006 |
| WO | WO 2006/088798 | 8/2006 |
| WO | WO 2006/088875 | 8/2006 |
| WO | WO 2006/091719 | 8/2006 |
| WO | WO 2006/094681 | 9/2006 |
| WO | WO 2006/113796 | 10/2006 |
| WO | WO 2006/131806 | 12/2006 |
| WO | WO 2007/022255 | 2/2007 |
| WO | WO 2007/050580 | 5/2007 |
| WO | WO 2007/062186 | 5/2007 |
| WO | WO 2007/092350 | 8/2007 |
| WO | WO 2007/098408 | 8/2007 |
| WO | WO 2007/103555 | 9/2007 |
| WO | WO 2007/110871 | 10/2007 |
| WO | WO 2007/111370 | 10/2007 |
| WO | WO 2007/111720 | 10/2007 |
| WO | WO 2007/128349 | 11/2007 |
| WO | WO 2007/133751 | 11/2007 |
| WO | WO 2008/054362 | 5/2008 |
| WO | WO 2008/113144 | 9/2008 |
| WO | WO 2009/060629 | 5/2009 |

OTHER PUBLICATIONS

International Search Report dated Jan. 19, 2010 for Application No. PCT/US209/059217.
Written Opinion dated Jan. 19, 2010 for Application No. PCT/US2009/059217.

METHOD FOR MAKING A MULTILAYER ADHESIVE LAMINATE

CROSS-REFERENCE TO RELATED APPLICATIONS

This application is a continuation of co-pending U.S. patent application Ser. No. 13/299,747, filed on Nov. 18, 2011; which is a continuation of U.S. patent application Ser. No. 12/571,560, filed on Oct. 1, 2009; which claims priority to U.S. Provisional Patent Application Ser. No. 61/102,223, filed on Oct. 2, 2008; the entire disclosures of which are hereby incorporated herein for all purposes.

FIELD OF THE INVENTION

This invention is in the field of pressure sensitive adhesive coatings.

BACKGROUND

Pressure-sensitive adhesive laminates are common in products from numerous industries, including the medical and consumer healthcare industries. Within these industries, pressure-sensitive adhesive laminates may be used for transdermal patches, medical tapes, wound dressings, and topical skin patches. While this section and the disclosure herein may focus on medical and consumer healthcare applications, it should be understood that this disclosure is not limited to these applications or industries.

A common process used to manufacture pressure-sensitive adhesive laminates involves a continuous solvent-based adhesive coating process. Such a process may employ any suitable type of solvent, including water. However, the thickness of the adhesive coating produced by such a process is limited. For instance, to achieve a thicker adhesive-coated product using a solvent-based adhesive coating processes, it is necessary to slow production speeds to give thicker adhesive coatings adequate drying time, or increase temperatures, which may cause the formation of surface imperfections. Alternatively, one may use such a process in batch mode to combine layers to produce thicker adhesive laminates. These approaches to producing thick or multilayer adhesive laminates are cost intensive and inefficient. Therefore, there is a need for a process that allows for continuous rapid manufacture of a relatively thick adhesive laminate.

SUMMARY

The processes described herein allow for continuous rapid manufacture of relatively thin adhesive coatings, where the thin coatings are continuously manufactured into a single thicker adhesive laminate.

In one embodiment, this disclosure pertains to a method of continuously manufacturing a multilayer pressure-sensitive adhesive laminate including the steps of: (1) producing a web having a first surface with an adhesive layer and a second surface with a release liner; (2) slitting the web longitudinally into a first section and a second section, each section having a first surface with an adhesive layer and a second surface with a release liner; (3) positioning the first section and second section so the adhesive layer of the first section faces the adhesive layer of the second section along the length of the first and second sections; and (4) laminating the first section and second section together such that the adhesive layers of the first and second sections are attached. The resultant laminate has two surfaces each having a release liner and an inner area having an adhesive layer.

In another embodiment, this disclosure pertains to a method of continuously manufacturing a multilayer pressure-sensitive adhesive laminate including the steps of: (1) producing a web having a first surface with an adhesive layer and a second surface with a release liner; (2) slitting the web longitudinally into a first section and a second section, each section having a first surface with an adhesive layer and a second surface with a release liner; (3) laminating a backing film to the adhesive layer of the first section; (4) removing the release liner of the laminate of step (3) and exposing the adhesive layer of the first section; (5) positioning the laminate of step (4) and the second section so the exposed adhesive layer of the laminate of step (4) faces the adhesive layer of the second section; and (6) laminating the second section to the laminate of step (4), wherein the adhesive layer of the laminate of step (4) is combined with the adhesive layer of the second section. The final laminate has one surface having a backing film, one surface having a release liner, and an inner area having an adhesive layer.

In another embodiment this disclosure pertains to a method of continuously manufacturing a multilayer pressure-sensitive adhesive laminate including the steps of: (1) producing a web having a first surface with an adhesive layer and a second surface with a release liner; (2) slitting the web longitudinally into a plurality of sections, each of the plurality of sections having a first surface with an adhesive layer and a second surface with a release liner; (3) laminating a backing film to the adhesive layer of a first section of the plurality of sections; (4) removing the release liner of the laminate of step (3) and exposing the adhesive layer associated with the first section; (5) positioning the laminate of step (4) and a next section of the plurality of sections so the exposed adhesive layer of the laminate of step (4) faces the adhesive layer of the next section; (6) laminating the next section to the laminate of step (4), wherein the adhesive layer of the laminate of step (4) is combined with the adhesive layer of the next section; (7) removing the release liner of the laminate of step (6) exposing the adhesive layer associated with the next section; and (8) repeating steps (5) through (7) to achieve a desired number of laminated layers; wherein step (7) is omitted with the final laminated section of the plurality of sections. The final laminate has one surface having a backing film, one surface having a release liner, and an inner area having an adhesive layer.

The above embodiments are exemplary only and should not be interpreted to limit the scope of this disclosure. It should be understood that this disclosure encompasses numerous embodiments, some of which are not explicitly disclosed within this section. Ultimately, the scope of this disclosure is defined by the broadest reading of the claims herein.

BRIEF DESCRIPTION OF THE DRAWINGS

The accompanying drawings are incorporated in and constitute a part of this specification. Together with the detailed description given below, the drawings serve to explain how the teachings of this application could be implemented. It should be understood that the teachings of this application are not limited to being implemented in the precise arrangements shown. In the drawings.

DETAILED DESCRIPTION

In discussing the figures, specific frame of reference conventions are designated, which includes describing an upward and downward orientation. When viewing the exemplary process figures (FIGS. 1B, 2B, and 3B), an upward orientation is associated with an object facing out-of-the-page, whereas a downward orientation is associated with an object facing into-the-page. When viewing the laminate schematic figures (FIGS. 1C-1D, 2C-2F, and 3C-3I), an upward orientation is associated with an object facing the top of the page, whereas a downward orientation is associated with an object facing the bottom of the page. These frame of reference conventions are used only for aiding in understanding the disclosure. In no sense should the disclosure be limited to such a frame of reference as other suitable manners of description fall within the scope of this disclosure.

Figure 1A:
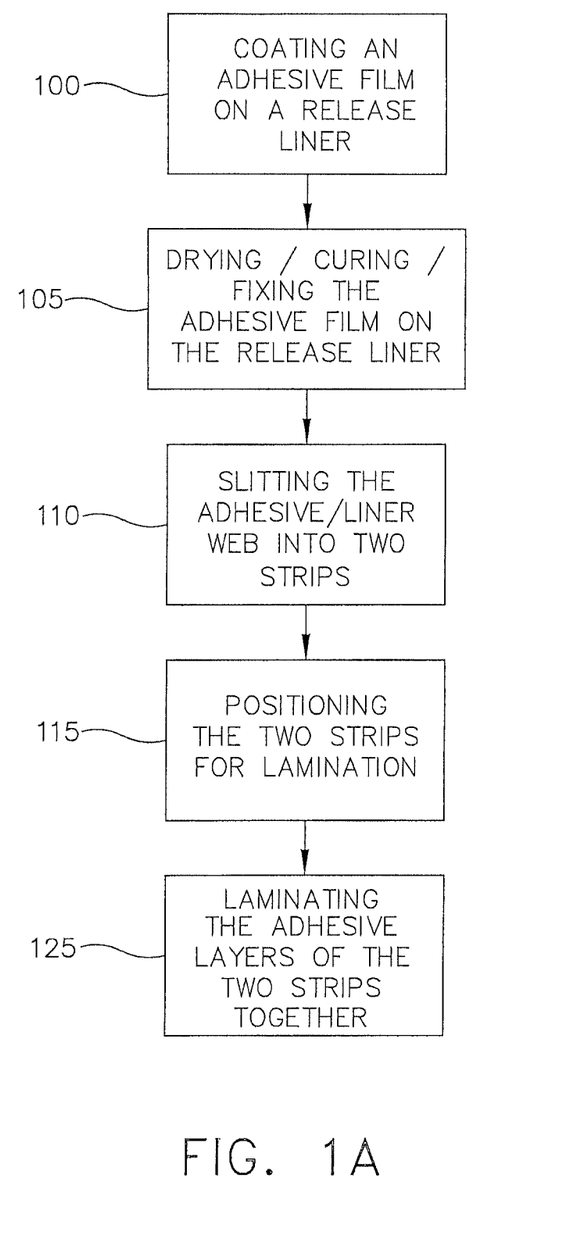
FIG. 1A depicts a flow diagram of a method to make a multilayer adhesive laminate having an adhesive coating between two release liners.

FIG. 1A describes a process for manufacturing a multilayer adhesive laminate by pairing two adhesive coatings between release liners. At step 100, a coating of adhesive is applied to a release liner, using any suitable coating method, to produce a coated web. Step 105 is a curing process, using any suitable method, where the adhesive-coated web is converted from a fluid to a fixed film. A suitable curing process may include, but is not limited to, a drying process. At step 110, the cured web is slit into two strips using any suitable slitting method. At step 115, the separate strips are directed through the process to orient the adhesive layers of the two strips such that they face one another in preparation for lamination. At step 125, the adhesive layers of the two strips are laminated together, using any suitable lamination method, to form a multilayer adhesive laminate having an inner adhesive layer surrounded on both sides by a release liner.

Figure 1B:
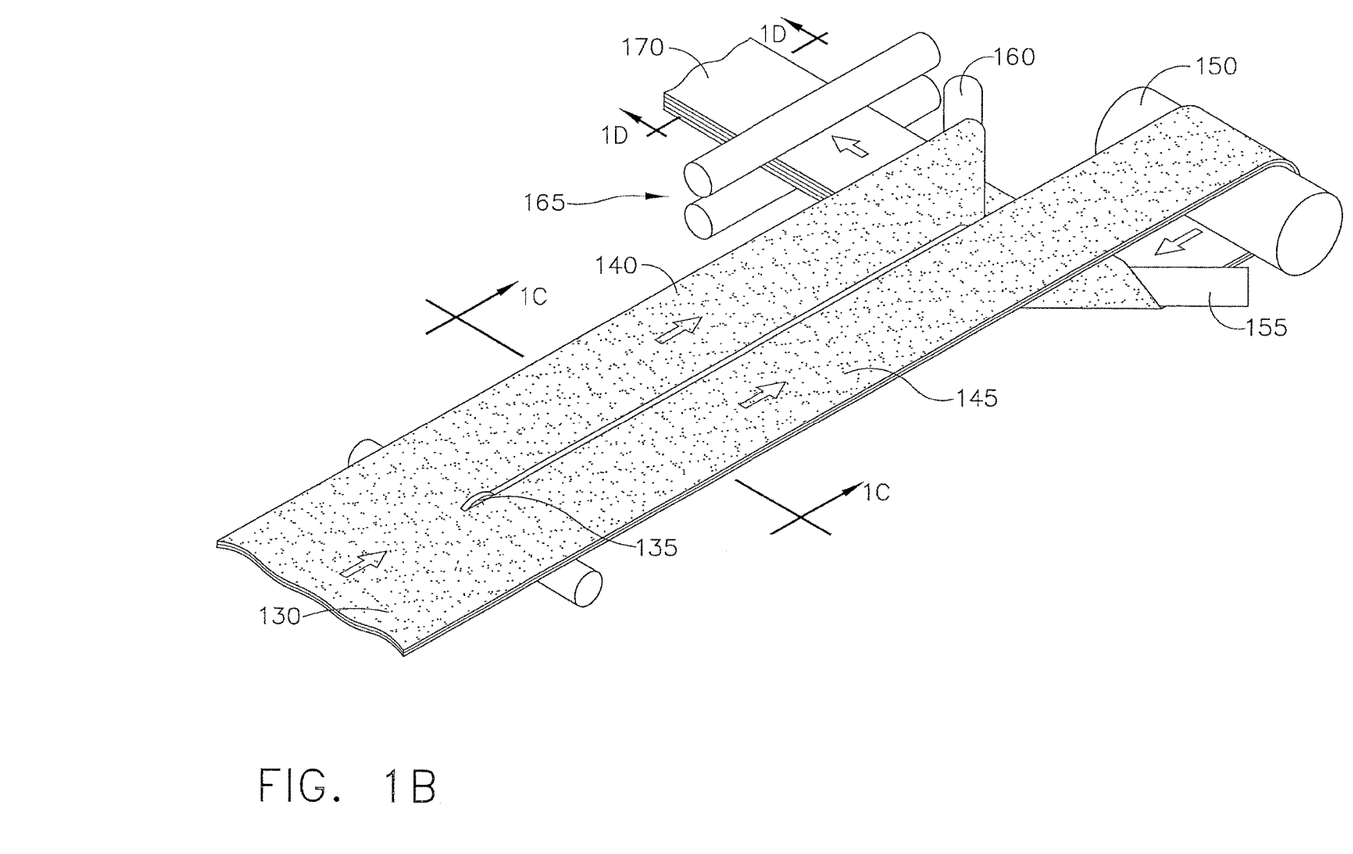
FIG. 1B depicts a schematic diagram of an exemplary process for the method shown in FIG. 1A.
Figure 1C:
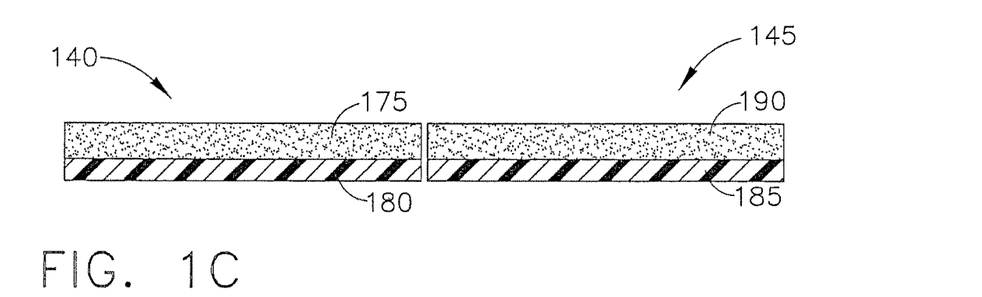
FIG. 1C depicts a cross-section view of the adhesive coated release liner strips used in the lamination process of FIG. 1B.

Referring to FIG. 1B, a schematic shows an exemplary way to direct the strips to achieve the multilayer adhesive laminate discussed in FIG. 1A. In FIG. 1B, web section 130 is the adhesive coated web after curing step 105 of FIG. 1A. Web section 130 travels through slitter 135 where web section 130 is divided into strip sections 140 and 145. Strip section 140 travels over 45-degree turning roller 160, which causes a change in the surface orientation of strip section 140, and causes strip section 140 to change its direction of travel by about 90-degrees. FIGS. 1B and 1C show that before strip section 140 passes over 45-degree turning roller 160, adhesive layer 175 of strip section 140 faces upward (and conversely the release liner 180 faces downward). After passing over 45-degree turning roller 160, adhesive layer 175 of strip section 140 faces downward (and conversely the release liner 180 faces upward).

Still referring to FIG. 1B, strip section 145 is directed to 90-degree turning roller 150, which causes a change in the surface orientation of strip section 145, and causes strip section 145 to reverse its direction of travel. As shown for FIGS. 1B and 1C, adhesive layer 190 of strip section 145 faces upward (and conversely the release liner 185 faces downward) before passing over 90-degree turning roller 150. After passing over 90-degree turning roller 150, adhesive layer 190 of strip section 145 faces downward (and conversely the release liner 185 faces upward). Strip section 145 is then directed to 45-degree turning roller 155, which causes a change in the surface orientation of strip section 145, and causes strip section 145 to change its direction of travel by about 90-degrees. As shown in FIG. 1B, 45-degree turning roller 155 is located such that after turning roller 155, strip section 145 aligns with strip section 140, and strip section 140 travels above strip section 145 in the same direction. Those of ordinary skill in the art will appreciate that heights of strip sections 140 and 145 may be manipulated by positioning turning rollers or web guides at different heights with respect to a common plane of reference. Furthermore, as shown in FIG. 1B, after passing over 45-degree turning roller 155, adhesive layer 190 of strip section 145 now faces adhesive layer 175 of strip section 140.

Figure 1D:
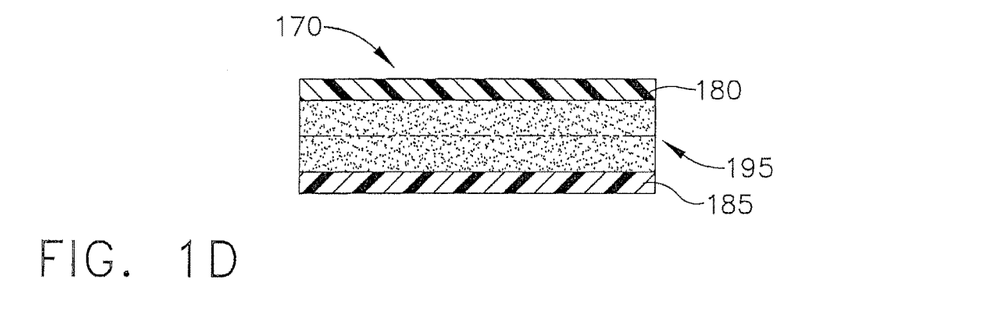
FIG. 1D depicts a cross-section view of the multilayer adhesive laminate produced in the lamination process of FIG. 1B.

Still referring to FIG. 1B, with strip sections 140 and 145 oriented as described above, strip sections 140 and 145 then pass through a lamination section 165. Lamination section 165 causes the adhesive layers 175 and 190, of strip sections 140 and 145 respectively, to join forming a multilayer adhesive laminate 170. As shown in FIGS. 1B and 1D, the multilayer adhesive laminate 170 has a combined adhesive layer 195, surrounded on either side by release liners 180 and 185. It should be noted that combined adhesive layer 195 is comprised of adhesive layer 175 of strip section 140 and adhesive layer 190 of strip section 145.

Figure 2A:
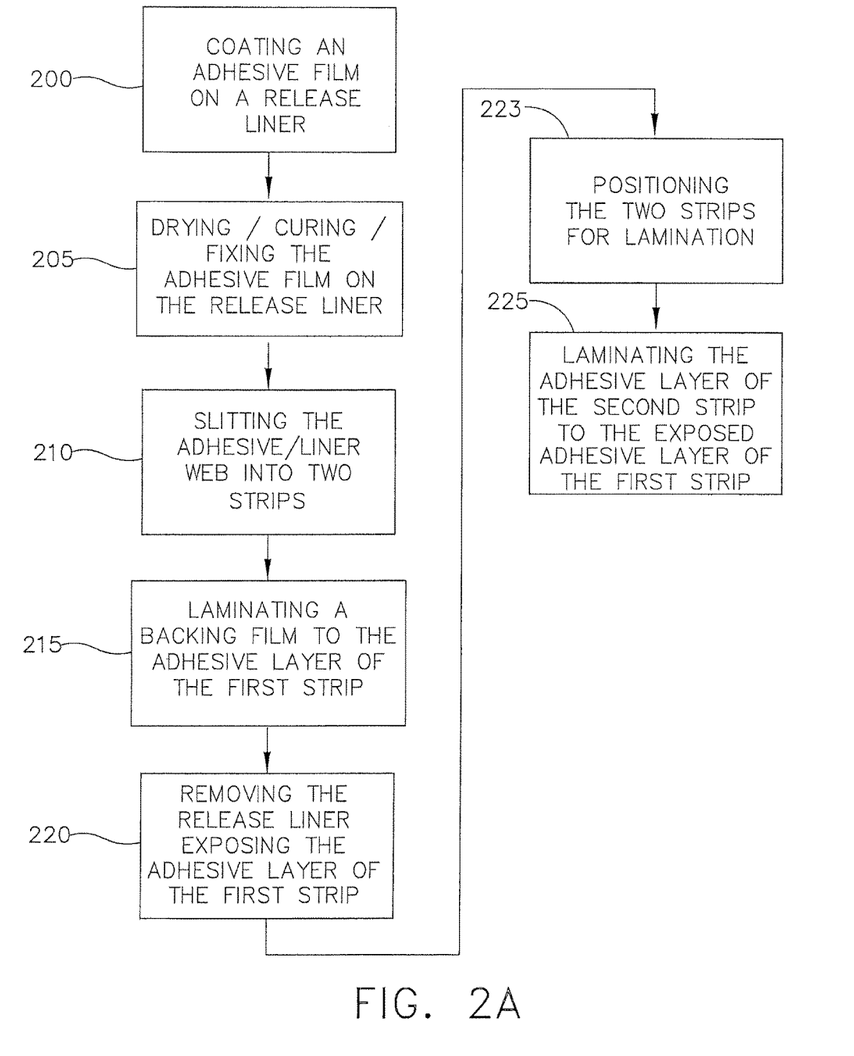
FIG. 2A depicts a flow diagram of a method to make a multilayer adhesive laminate having an adhesive coating between a release liner and a backing film.

Now referring to FIG. 2A, a process is shown for manufacturing a multilayer adhesive laminate by pairing two adhesive coatings between a release liner and a backing film. At step 200, an adhesive coating is applied to a release liner using any suitable coating method. At step 205, the web containing the adhesive coating and release liner is cured using any suitable method. At step 210, the web is slit into two strips using any suitable slitting method. At step 215 a backing film is attached to the adhesive layer of one of the strips. From this same strip, at step 220, the release liner is removed, thus exposing the adhesive layer of the strip opposite the side of the backing film. At step 223, the separate strips are then directed through the process to orient the adhesive layers of the two strips such that they face one another in preparation for lamination. At step 225 the adhesive layers of the two strips are laminated together using any suitable lamination method to form a multilayer adhesive laminate.

Figure 2B:
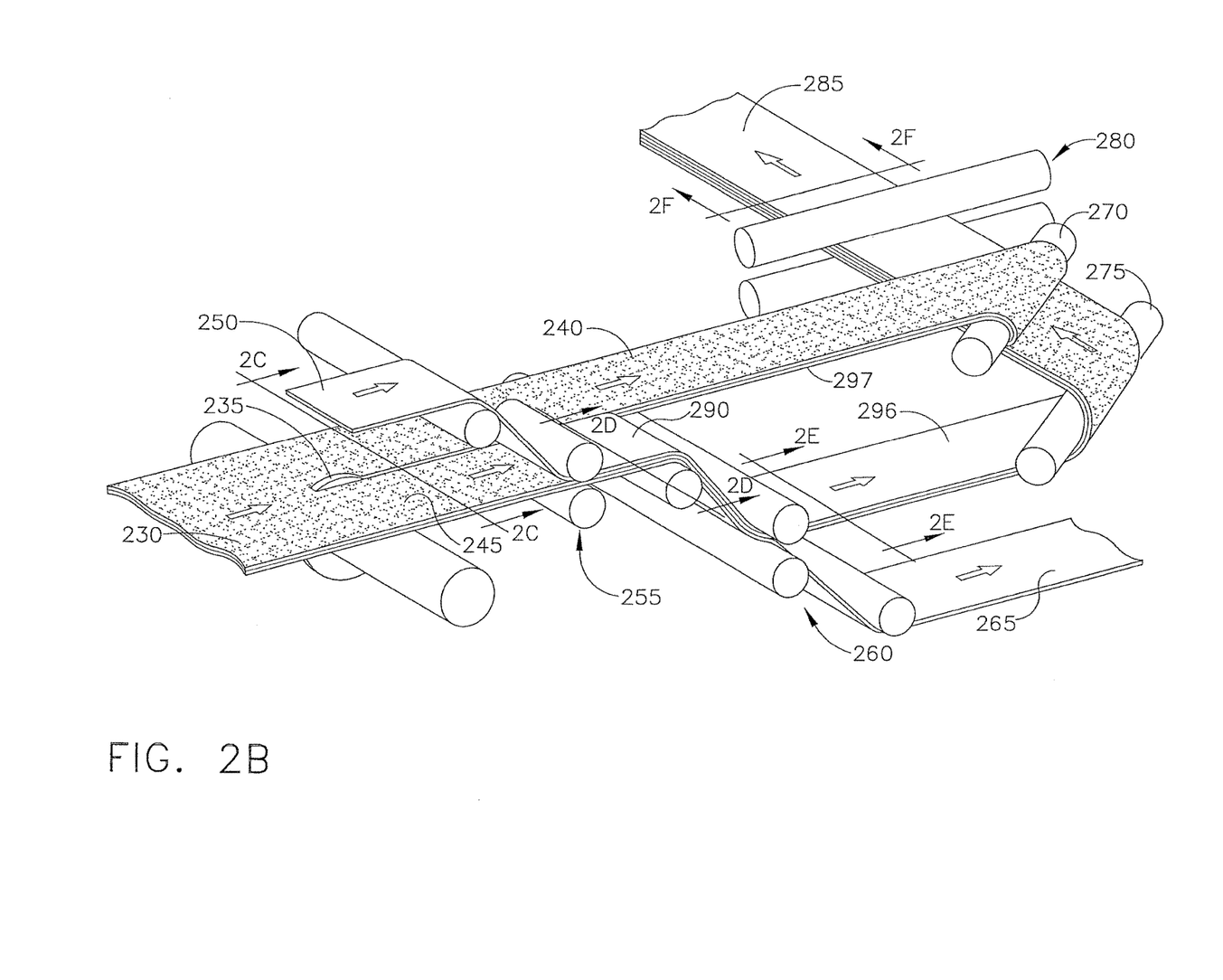
FIG. 2B depicts a schematic diagram of an exemplary process for the method shown in FIG. 2A.
Figure 2C:
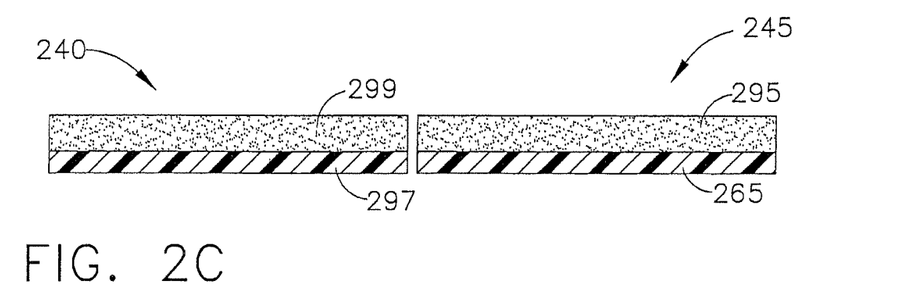
FIG. 2C depicts a cross-section view of the adhesive coated release liner strips used in the lamination process of FIG. 2B.
Figure 2D:
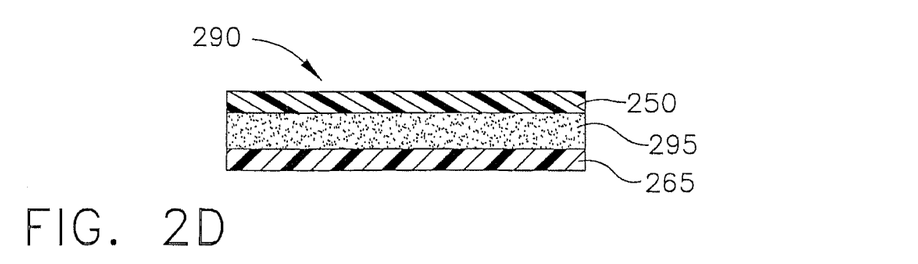
FIG. 2D depicts a cross-section view of the adhesive coated release liner strip containing the backing film as used in the lamination process of FIG. 2B.
Figure 2E:
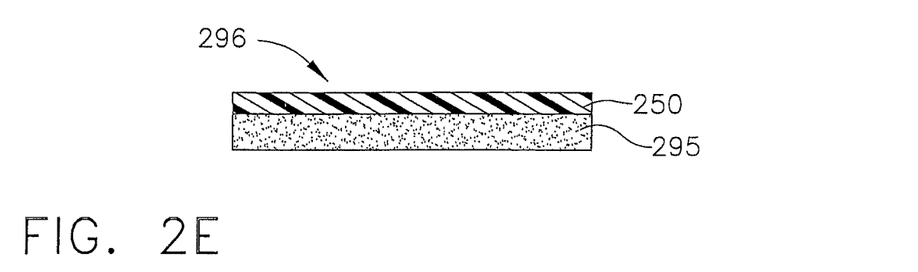
FIG. 2E depicts a cross-section view of the strip of FIG. 2D with the release liner removed.

Referring to FIGS. 2B-2F, a schematic shows an exemplary way to direct the strips to achieve the multilayer adhesive laminate discussed in FIG. 2A. In FIG. 2B, web section 230 is the adhesive-coated web after curing step 205 of FIG. 2A. Web section 230 travels through slitter 235 where web section 230 is divided into strip sections 240 and 245. Strip section 245 travels to backing film application section 255, where backing film 250 is attached to adhesive layer 295 of strip section 245 to produce strip section 290 having a backing film 250, an adhesive layer 295, and a release liner 265 as shown in FIGS. 2B and 2D. Strip section 290 then travels to a release liner removal section 260. Release liner 265 is removed from strip section 290 to produce strip section 296. As shown in FIG. 2E, strip section 296 has backing film 250 on top of adhesive layer 295, which now has an exposed adhesive surface where release liner 265 was formerly positioned. Strip section 296 travels over 45-degree turning roller 275, which causes a change in the surface orientation of strip section 296, and causes strip section 296 to change its direction of travel by about 90-degrees. FIGS. 2B and 2E show that before strip section 296 passes over 45-degree turning roller 275, backing film 250 of strip section 296 faces upward (and conversely the adhesive layer 295 faces downward). After passing over 45-degree turning roller 275, backing film 250 of strip 296 faces downward (and conversely the adhesive layer 295 faces upward).

Still referring to FIGS. 2B-2F, strip section 240 is directed into 45-degree turning roller 270, which causes a change in the surface orientation of strip section 240, and causes strip section 240 to change its direction of travel by about 90-degrees. FIGS. 2B and 2C show that before strip section 240 passes over 45-degree turning roller 270, adhesive layer 299 of strip section 240 faces upward (and conversely the release liner 297 faces downward). After passing over 45-degree turning roller 270, adhesive layer 299 of strip section 240 faces downward (and conversely the release liner 297 faces upward). As shown in FIG. 2B, 45-degree turning rollers 270 and 275 are located such that strip sections 240 and 296 align, and such that strip section 240 is traveling above strip section 296 and in the same direction and speed. Those of ordinary skill in the art will appreciate that heights of strip sections 240 and 296 may be manipulated by positioning turning rollers or web guides at different heights with respect to a common plane of reference. Furthermore, as shown in FIGS. 2B, 2C, and 2E, after passing over 45-degree turning roller 270, adhesive layer 299 of strip section 240 is now oriented facing adhesive layer 295 of strip section 296.

Figure 2F:
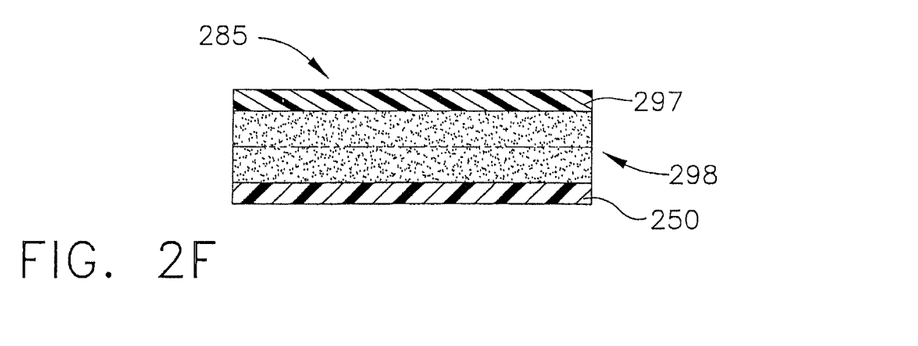
FIG. 2F depicts a cross-section view of the multilayer adhesive laminate produced in the lamination process of FIG. 2B.

Still referring to FIGS. 2B-2F, with strip sections 240 and 296 oriented as described above, strip sections 240 and 296 then pass through a lamination section 280. Lamination section 280 causes the adhesive layers of strip sections 240 and 296, to join forming a multilayer adhesive laminate 285. As shown in FIGS. 2B and 2F, the multilayer adhesive laminate 285 has a combined adhesive layer 298 surrounded on one side by backing film 250 and one the other side by release liner 297. It should be noted that combined adhesive layer 298 is comprised of adhesive layer 299 of strip section 240 and adhesive layer 295 of strip section 245.

Figure 3A:
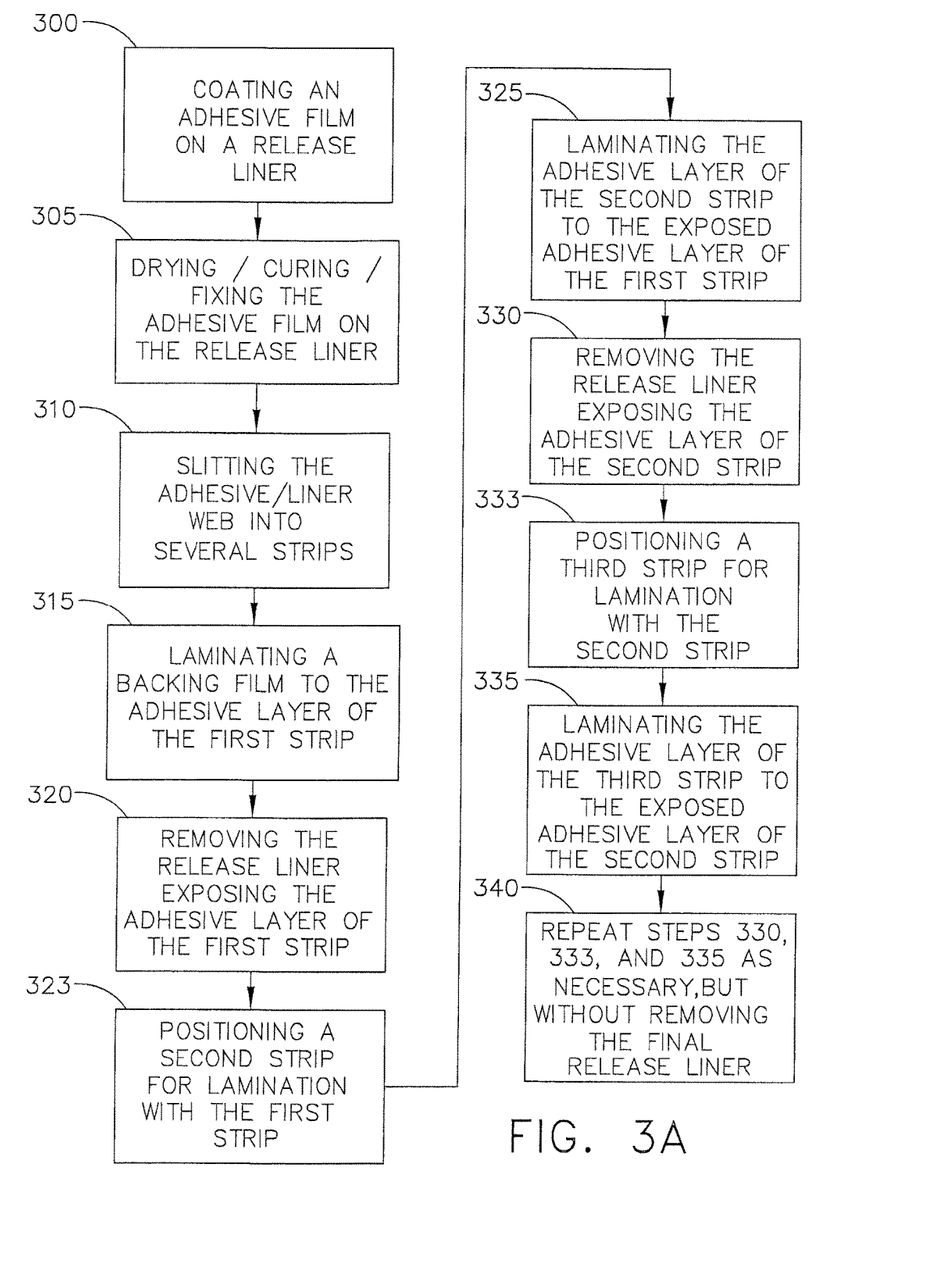
FIG. 3A depicts a flow diagram of a method to make a multilayer adhesive laminate having an adhesive coating between a release liner and a backing film.

Now referring to FIG. 3A, a process is shown for manufacturing a multilayer adhesive laminate by combining a multitude of adhesive coatings between a single release liner and single backing film. At step 300, an adhesive coating is applied to a release liner using any suitable coating method. At step 305, the web containing the adhesive-coating and release liner is cured using any suitable method. At step 310 the web is slit into several strips using any suitable slitting method. At step 315 a backing film is attached to the adhesive layer of a first strip. From this first strip, at step 320, the release liner is removed, thus exposing the adhesive layer of the first strip, opposite the side of the backing film. At step 323, a second strip is then directed through the process to orient its adhesive layer such that it faces the exposed adhesive layer of the first strip. At step 325, the adhesive layer of the second strip is laminated to the exposed adhesive layer of the first strip using any suitable lamination process. At step 330, the release liner of the second strip is removed, thus exposing the adhesive layer of the second strip, opposite the side laminated to the first strip. At step 333, a third strip is then directed through the process to orient its adhesive layer such that it faces the exposed adhesive layer of the second strip. At step 335, the adhesive layer of the third strip is laminated to the exposed adhesive layer of the second strip using any suitable lamination process. At step 340, steps 330, 333, and 335 are repeated with the next available strip for lamination. However, step 340 concludes by not removing the release liner of the final laminated strip, thus forming the multilayer adhesive laminate.

Figure 3B:
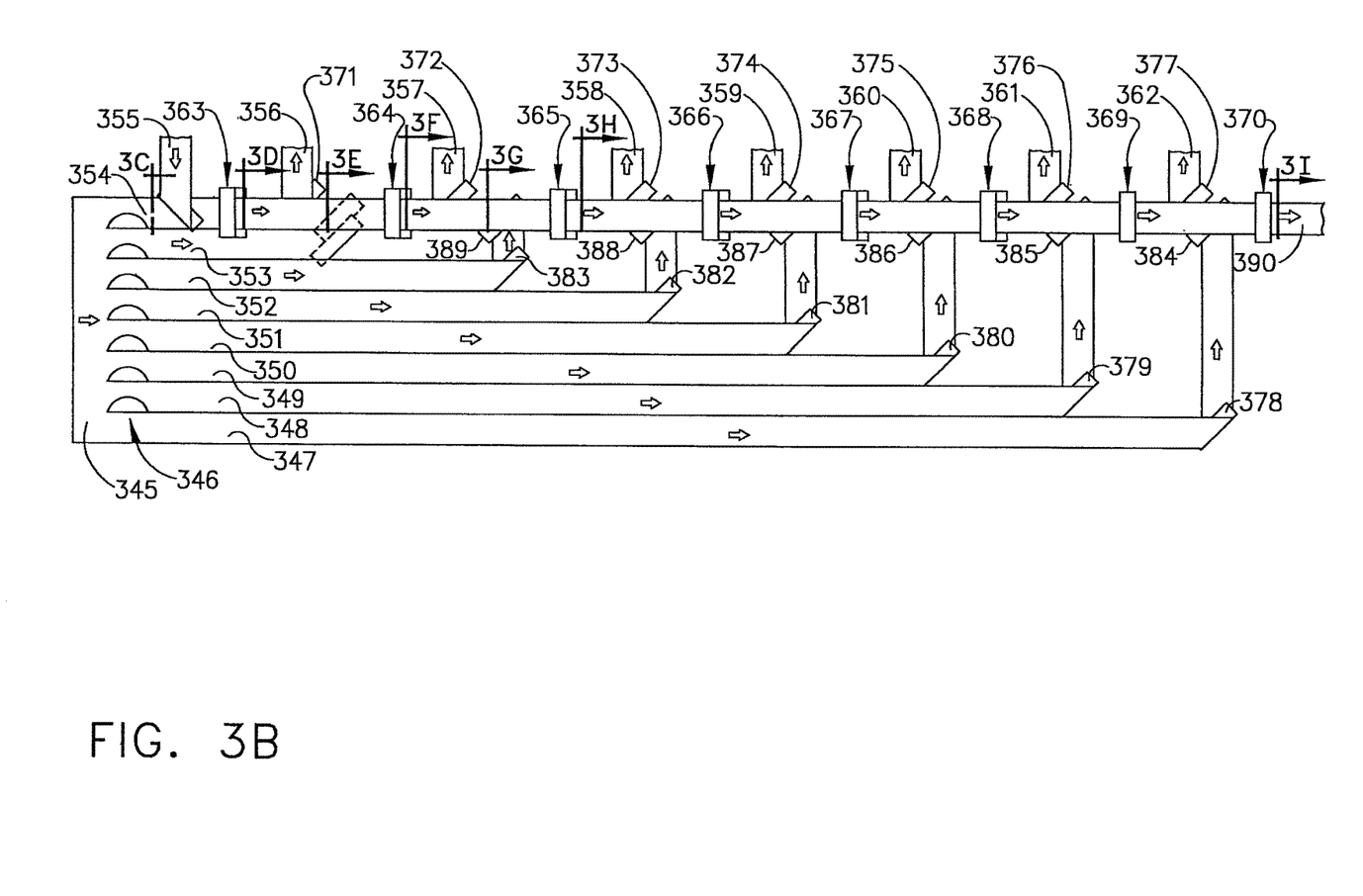
FIG. 3B depicts a schematic diagram of an exemplary process for the method shown in FIG. 3A.
Figure 3C:
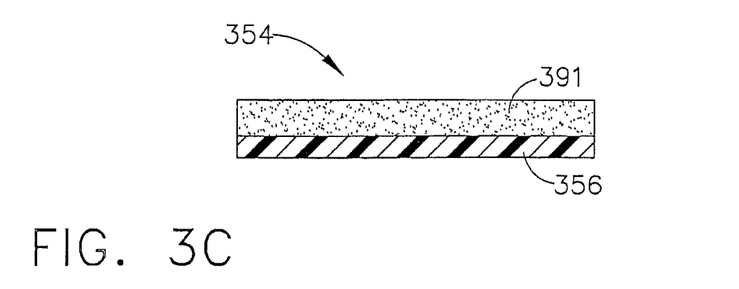
FIG. 3C depicts a cross-section view of the adhesive coated release liner strips used in the lamination process of FIG. 3B.

Referring to FIGS. 3B-3H, a schematic shows an exemplary way to direct the strips to achieve the multilayer adhesive laminate discussed in FIG. 3A. In FIG. 3B, web section 345 is the adhesive coated web after curing step 305 of FIG. 3A. Web section 345 travels through slitter section 346 where web section 345 is divided into a plurality of strip sections 347, 348, 349, 350, 351, 352, 353, and 354. Strip section 354 has an adhesive layer 391 on a release liner 356 as shown in FIG. 3C. Each of strip sections 347, 348, 349, 351, 352, and 353 have a similar adhesive layer on release liner structure as shown in FIG. 3C with respect to strip section 354.

Figure 3D:
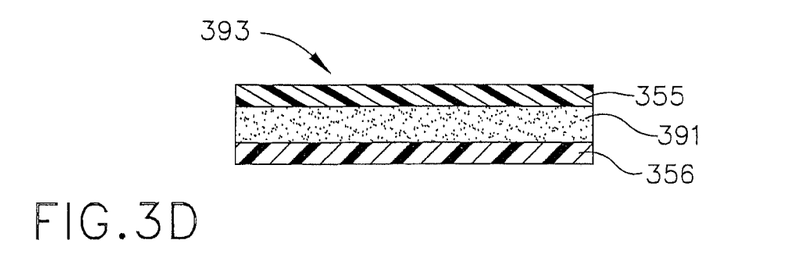
FIG. 3D depicts a cross-section view of the adhesive coated release liner strip containing the backing film as used in the lamination process of FIG. 3B.
Figure 3E:
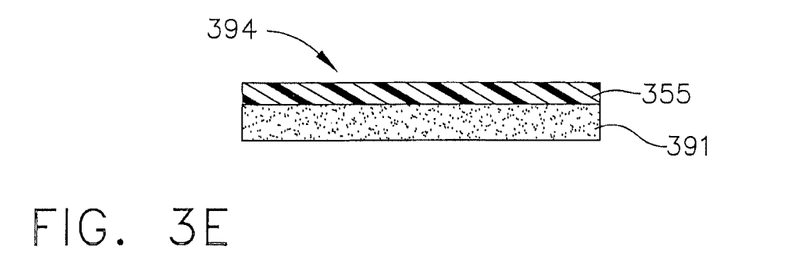
FIG. 3E depicts a cross-section view of the strip of FIG. 3D with the release liner removed.

Still referring to FIGS. 3B-3H, strip section 354 travels to backing film application section 363, where backing film 355 is attached to adhesive layer 391 of strip section 354 to produce a strip section 393 having a backing film 355, an adhesive layer 391, and a release liner 356 as shown in FIG. 3D. Strip section 393 then travels to a release liner removal section 371. Release liner 356 is removed from strip section 393 to produce strip section 394. As shown in FIG. 3E, strip section 394 has backing film 355 on adhesive layer 391, which now has an exposed adhesive surface where release liner 356 was formerly positioned.

Strip section 353 travels into 45-degree turning roller (shown in phantom in drawing), which causes a change in the surface orientation of strip section 353, and causes strip section 353 to change its direction of travel by about 90-degrees. FIG. 3B shows that before strip section 353 passes over the 45-degree turning roller, the adhesive layer of strip section 353 faces upward (and conversely the release liner 357 faces downward). After passing over the 45-degree turning roller, the adhesive layer of strip section 353 faces downward (and conversely the release liner 357 faces upward). Strip section 353 continues into another 45-degree turning roller (shown in phantom in drawing), which again causes a change in the surface orientation of strip section 353, and causes strip section 353 to change its direction of travel by about 90-degrees. FIG. 3B shows that before strip section 353 passes over the second 45-degree turning roller, the adhesive layer of strip section 353 faces downward (and conversely the release liner 357 faces upward). After passing over the second 45-degree turning roller, the adhesive layer of strip section 353 faces upward (and conversely the release liner 357 faces downward). As shown in FIGS. 3B and 3E, the 45-degree turning rollers that guide strip section 353 are located such that, at the exit of the second 45-degree turning roller, strip section 353 aligns with strip section 394, and strip section 353 is traveling below strip section 394 in the same direction and speed. Those of ordinary skill in the art will appreciate that heights of strip sections 353 and 394 may be manipulated by positioning turning rollers or web path guides at different heights with respect to a common plane of reference. Furthermore, after passing over the second 45-degree turning roller, the adhesive layer of strip section 353 faces the exposed adhesive layer 391 of strip section 394.

Figure 3F:
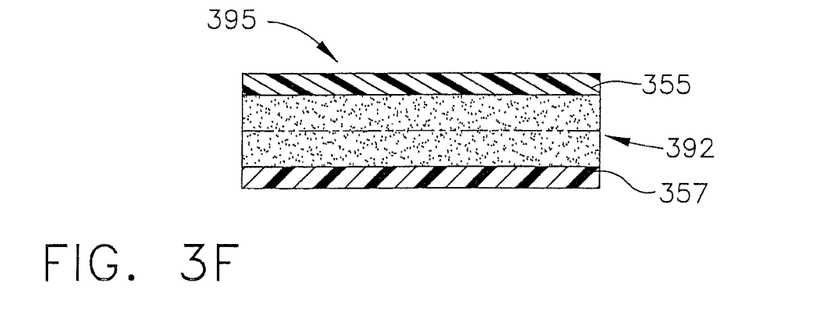
FIG. 3F depicts a cross-section view of the strip of FIG. 3E after an additional strip of adhesive coated release liner has been laminated to the strip of FIG. 3E.

Still referring to FIGS. 3B-3H, with strip sections 353 and 394 oriented as described above, strip sections 353 and 394 then pass through a lamination section 364. Lamination section 364 causes the adhesive layers of strip sections 353 and 394, to join together forming a strip section 395 as shown in FIG. 3F. Strip section 395 has a combined adhesive layer 392 surrounded on one side by backing film 355 and on the opposite side by release liner 357. It should be noted that combined adhesive layer 392 is comprised of adhesive layer 391 of strip section 394 and the adhesive layer of strip section 353.

Figure 3G:
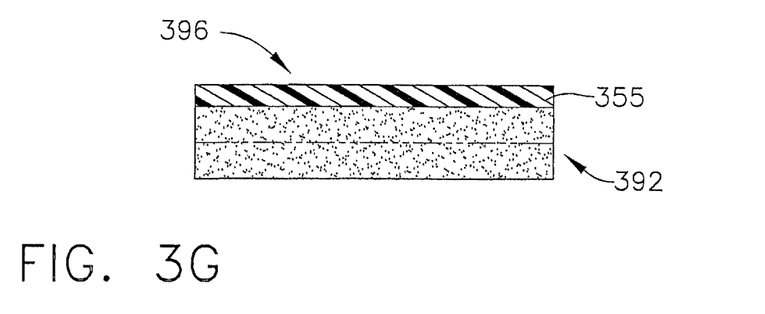
FIG. 3G depicts a cross-section view of the strip of FIG. 3F with the release liner removed.

Still referring to FIGS. 3B-3H, strip section 395 then travels to a release liner removal section 372. Release liner 357 is removed from strip section 395 to produce strip section 396. As shown in FIG. 3G, strip section 396 has backing film 355 on top of combined adhesive layer 392, which now has an exposed adhesive surface where release liner 357 was formerly positioned.

Strip section 352 travels into 45-degree turning roller 383, which causes a change in the surface orientation of strip section 352, and causes strip section 352 to change its direction of travel by about 90-degrees. FIG. 3B shows that before strip section 352 passes over 45-degree turning roller 383, the adhesive layer of strip section 352 faces upward (and conversely the release liner 358 faces downward). After passing over 45-degree turning roller 383, the adhesive layer of strip section 352 faces downward (and conversely the release liner 358 faces upward). Strip section 352 continues into another 45-degree turning roller 389, which again causes a change in the surface orientation of strip section 352, and causes strip section 352 to change its direction of travel by about 90-degrees. FIG. 3B shows that before strip section 352 passes over 45-degree turning roller 389, the adhesive layer of strip section 352 faces downward (and conversely the release liner 358 faces upward). After passing over 45-degree turning roller 389, the adhesive layer of strip section 352 faces upward (and conversely the release liner 358 faces downward). As shown in FIGS. 3B and 3G, 45-degree turning rollers 383, 389 that guide strip section 352 are located such that, at the exit of 45-degree turning roller 389, strip section 352 aligns with strip section 396, and strip section 352 is traveling below strip section 396 in the same direction and speed. Those of ordinary skill in the art will appreciate that heights of strip sections 352 and 396 may be manipulated by positioning turning rollers or web path guides at different heights with respect to a common plane of reference. Furthermore, after passing over 45-degree turning roller 389, the adhesive layer of strip section 352 faces the exposed adhesive layer 392 of strip section 396.

Figure 3H:
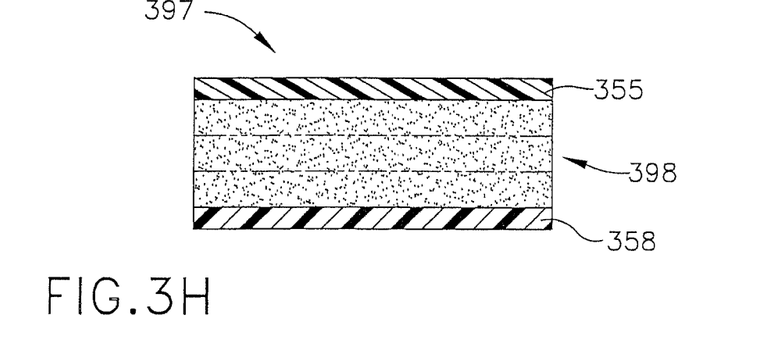
FIG. 3H depicts a cross-section view of the strip of FIG. 3G after an additional strip of adhesive coated release liner has been laminated to the strip of FIG. 3G.

Still referring to FIGS. 3B-3H, with strip sections 352 and 396 oriented as described above, strip sections 352 and 396 then pass through a lamination section 365. Lamination section 365 causes the adhesive layers of strip sections 352 and 396, to join forming a strip section 397 as shown in FIG. 3H. Strip section 397 has a combined adhesive layer 398 surrounded on one side by backing film 355 and on the opposite side by release liner 358. It should be noted that combined adhesive layer 398 is comprised of adhesive layer 392 of strip section 396 and the adhesive layer of strip section 352.

Figure 3I:
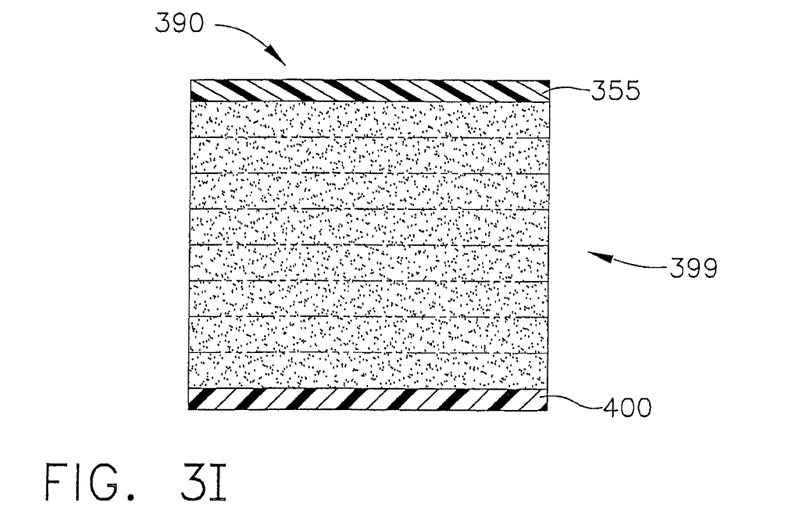
FIG. 3I depicts a cross-section view of the multilayer adhesive laminate produced in the lamination process of FIG. 3B.

As shown in FIGS. 3A and 3B, the process described in the preceding paragraphs repeats to achieve the desired laminate thickness. More specifically, release liner 358 of strip section 397 is removed and strip section 351 is positioned using 45-degree turning rollers for lamination. As shown in FIG. 3B, after final strip section 347 is laminated to the intermediate product, the release liner of strip section 347 is maintained on the laminate to produce the final multilayer adhesive laminate 390 as shown in FIGS. 3B and 3I. The final multilayer adhesive laminate 390 has a combined adhesive layer 399 surrounded on one side by backing film 355 and on the other side by release liner 400. It should be noted that combined adhesive layer 399 is comprised of the adhesive layers of strip sections 354, 353, 352, 351, 350, 349, 348, and 347.

While the above paragraphs have described several product features, this disclosure should not be limited to the precise features shown and described. For example, the adhesive coating disclosed may be of any of several types. For instance, the adhesive coating may be a solvent based adhesive coating for use in a transdermal or topical medical patch. In such examples, the adhesive coating may contain medicinal formulations for the treatment of certain ailments. By way of example and not limitation, to treat skin pain or discomfort, lidocaine may be combined with the adhesive to create a skin treatment patch. Those of ordinary skill in the art will appreciate that the adhesive may be combined with any suitable medicinal formulation, where topical or transdermal drug delivery is desired.

Additional medical related applications for a multilayer adhesive laminate as disclosed herein may include medical tapes, wound dressings, ostomy adhesives, and numerous others. Similarly, the multilayer adhesive laminate disclosed herein, may have applications in other industries where a thick coating of pressure-sensitive adhesive is desirable; for example, applications may exist in consumer products, automotive, and home improvement industries.

Some additional product features described include release liners and backing films. It should be understood that this disclosure shall encompass any variety of release liners and backing films suitable for adhering to an adhesive coating. By way of example only, release liners and backing films may be manufactured from natural or synthetic fibers that may be woven, nonwoven, melt cast, or extruded. Furthermore, a combination of natural or synthetic fibers may be used. Those of ordinary skill in the art will appreciate the variety of materials suitable for use as both release liners and backing films.

The above disclosure also describes several process features, and the disclosure should not be limited to the precise process features shown or described. For example, several web-guiding structures are disclosed including 45-degree and 90-degree turning rollers. It should be understood, that in some embodiments such turning rollers may be driven or braked, while in other embodiments such turning rollers may be freely rotating. Still in other embodiments, turning rollers may be interchanged with turning or guide bars that do not rotate. Similarly, the precise degrees specified for the turning rollers are not required and may be substituted with turning rollers having other degree configurations.

Some additional process features described include coating, curing, slitting, and laminating processes. It should be understood that this disclosure is not intended to be limited to a specific method for conducting any of these processes. For example, several types of coating, curing, slitting, and laminating processes may be compatible with this disclosure. By way of example only, the adhesive coating may be accomplished in a spray application, a metered roller application, or any other suitable coating method. By way of example only, the curing process may be accomplished using a steam-filled-can drying system, a through-air drying system, a radiation curing system, or any other suitable method. By way of example only, the slitting process may be accomplished using a slitting blade that may be comprised of a metal or ceramic, a rotating slitting wheel, an air or water jet, or any other suitable slitting method. By way of example only, the laminating process may be accomplished by compressing the laminate layers between two rollers, by ultrasonic bonding, by chemical adhesion, or any other suitable laminating method. Those of ordinary skill in the art will appreciate the variety of methods suitable for use in coating, curing, slitting, and laminating.

Having shown and described various embodiments, further adaptations of the methods and systems described herein may be accomplished by appropriate modifications by one of ordinary skill in the art without departing from the scope of this disclosure. Several of such potential modifications have been mentioned, and others will be apparent to those skilled in the art. For instance, the examples, embodiments, geometries, materials, dimensions, ratios, steps, and the like discussed above are illustrative and are not required. Accordingly, the scope of the present invention should be considered in terms of whatever claims recite the invention, and is understood not to be limited to the details of structure and operation shown and described in the description.

What is claimed is:

1. A method of continuously manufacturing a multilayer pressure-sensitive adhesive laminate comprising the steps of:
   a. producing a web comprising a pressure-sensitive adhesive layer;
   b. slitting the web longitudinally into a first section and a second section; each section including a portion of the pressure-sensitive adhesive layer; wherein the first section and the second section are of substantially the same size; and
   c. laminating the first section and second section together such that the adhesive layers of the first and second sections are joined to form a combined adhesive layer.

2. The method of claim 1, comprising the step of positioning the first section and second section so the adhesive layer of the first section faces the adhesive layer of the second section along the length of the first and second sections.

3. The method of claim 2, wherein the act of positioning the first and second sections comprises turning a select one or both of the first section and the second section one or more times, such that the second section aligns with the first section with the adhesive layers of the first and second sections facing each other while traveling in the same direction.

4. The method of claim 3, wherein a select one or both of the first section and the second section are directed over one or more rollers, wherein the one or more rollers cause the select one or both of the first section and the second section to change direction of travel.

5. The method of claim 3, wherein the first section is directed over an about 45-degree turning roller, wherein the second section is directed over an about 90-degree turning roller, and wherein the second section is further directed over an about 45-degree turning roller.

6. The method of claim 3, wherein the first section is directed over one or more about 45-degree turning rollers, wherein the second section is directed over one or more about 45-degree turning rollers.

7. The method of claim 3, wherein the first section and second section are turned an unequal number of times.

8. A method of continuously manufacturing a multilayer pressure-sensitive adhesive laminate comprising the steps of:
   a. producing a web comprising a pressure-sensitive adhesive layer;
   b. slitting the web longitudinally into a first section and a second section; each section including a portion of the pressure-sensitive adhesive layer; wherein the first section and the second section are of substantially the same size;
   c. laminating a material to a first surface of the adhesive layer of the first section; wherein the material and the first surface of the adhesive layer of the first section are directly attached to each other; and
   d. laminating the adhesive layer of the second section to a second surface of the adhesive layer of the first section; wherein the adhesive layer of the second section and the second surface of the adhesive layer of the first section are joined to form a combined adhesive layer.

9. The method of claim 8, wherein the act of laminating the second section comprises turning a select one or both of the first section and the second section one or more times, such that the second section aligns with the first section with the adhesive layer of the second section facing the second surface of the adhesive layer of the first section.

10. The method of claim 9, wherein the second section is directed over an about 45-degree turning roller, wherein the first section with the material is directed over an about 45-degree turning roller.

11. The method of claim 9, wherein the first section and the second section are turned an equal number of times before laminating the second section to the second surface of the adhesive layer of the first section.

12. A method of continuously manufacturing a multilayer pressure-sensitive adhesive laminate comprising the steps of:
- a. coating a release liner with an adhesive layer;
- b. slitting the combined release liner and adhesive layer longitudinally into a first section and a second section; each section including a portion of the adhesive layer; wherein the first section and second section are of substantially the same size; and
- c. laminating the first section and second section together such that the adhesive layers of the first and second sections are joined to form a combined adhesive layer.

* * * * *